United States Patent [19]

Dyke

[11] Patent Number: 4,515,841
[45] Date of Patent: May 7, 1985

[54] PORE FORMING STERILIZATION BAG

[75] Inventor: Denis G. Dyke, Edinboro, Pa.

[73] Assignee: American Sterilizer Company, Erie, Pa.

[21] Appl. No.: 567,234

[22] Filed: Dec. 30, 1983

[51] Int. Cl.³ .............................................. B32B 1/02
[52] U.S. Cl. .................................... 428/35; 428/338; 428/913; 521/61
[58] Field of Search ................. 521/61; 220/DIG. 30; 383/1; 422/26; 428/35, 338, 542.8, 913

[56] References Cited

U.S. PATENT DOCUMENTS 3,992,496  11/1976  Matsunaga et al. ................. 521/61
4,118,438  10/1978  Matsui et al. ...................... 428/338
4,384,023   5/1983  Okamura et al. ................... 428/338

Primary Examiner—William J. Van Balen
Attorney, Agent, or Firm—Robert D. Yeager; Christine Ethridge; Andrew Cornelius

[57] ABSTRACT

A receptacle for handling contaminated waste for sterilization and subsequent disposal which is a pore forming sterilization bag made from a thermoplastic resin which has been embedded with either soluble materials or melt materials which respond to the temperature and moisture of steam sterilization to form pores in the bag, thus permitting the entrance of sterilant and the exit of air for sterilization of the waste. The melt materials are low molecular weight polymers such as carbowaxes. The soluble materials can be either organic or inorganic materials such as polyvinyl alcohol, polyvinyl acetate, polyvinyl pyrrolidone and various inorganic salts, such as sodium chloride.

10 Claims, 4 Drawing Figures

Fig. 1.
Fig. 2.
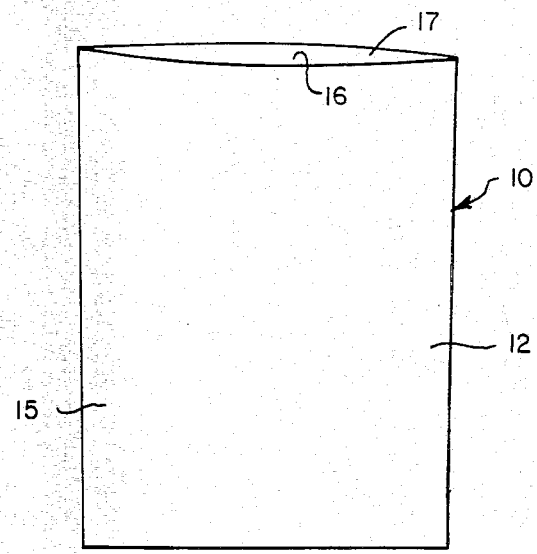
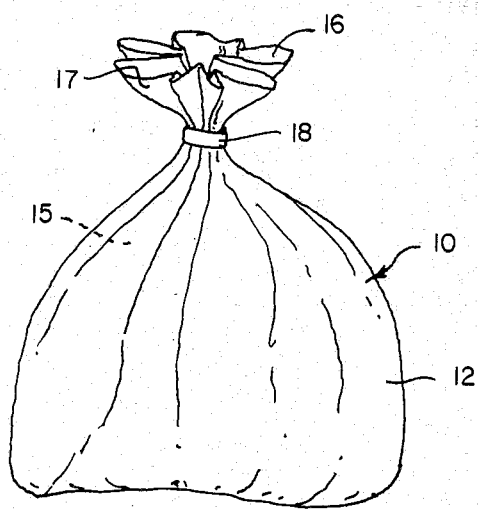
Fig. 3.
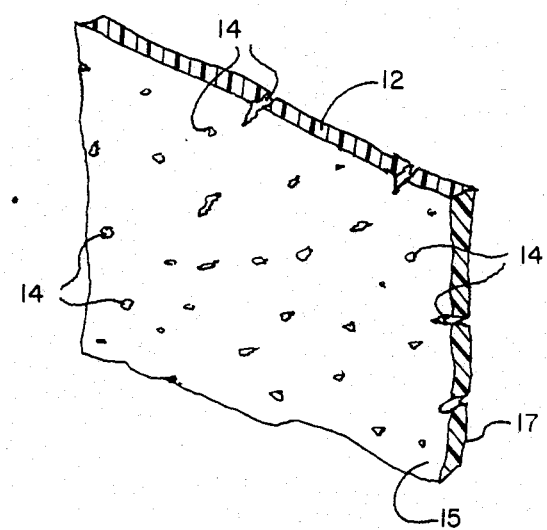
Fig. 4.
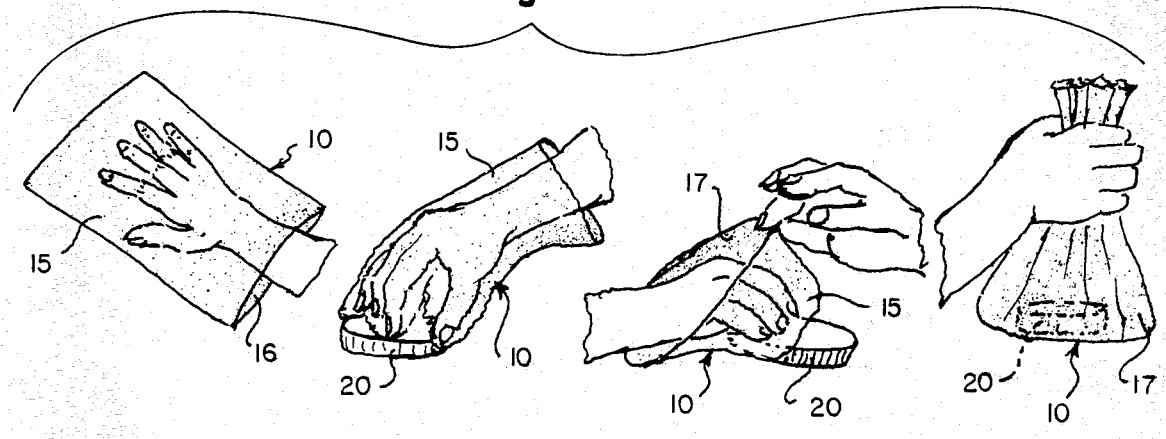

PORE FORMING STERILIZATION BAG

BACKGROUND OF THE INVENTION

1. Field of the Invention

The present invention relates to receptacles for handling contaminated waste for sterilization and subsequent disposal, more particularly to pore forming sterilization bags.

2. Description of the Prior Art

Throughout hospitals and research laboratories where infectious patient and animal wastes and tissue samples are handled, such materials, the container used to collect them and certain of the equipment used to test them must be disposed of or prepared for reuse. To prevent the potential spread of infection, such items must be sterilized. Sterilization containers and bags for this purpose are known in the art. The conventional biohazard bags are fabricated from continuous thermoplastic material, usually polypropylene and are impervious to steam or other sterilants. The bags, therefore, must be partially opened during the sterilization process and water must be added to them to generate the required steam. Opening such contaminated bags in an attempt to achieve sterilization is a dangerous practice which exposes the worker and the surrounding environment to the infectious contents. Sterilization of the waste items is often inadequate.

Schuster U.S. Pat. No. 4,270,658 discloses a sterilization pouch which has small ruptures on its inner surface which permit the entrance and exit of vapors during sterilization. The ruptures are mechanically produced during fabrication of the pouch. The pouch has a second outer layer of medical grade paper which is vapor permeable.

Moffet et al. U.S. Pat. No. 2,633,284 discloses a package for cooking which has preformed perforations of the surface which are covered with paraffin wax. The wax melts during cooking to expose the preformed perforations. Packages having pores are also disclosed by U.S. Pat. Nos. 3,093,335 and 3,887,072.

Preformed pores add to the expense of fabrication because of the added equipment and steps required. Furthermore, the preformed pores must be covered with a bacteria impervious material prior to sterilization to prevent the potential spread of infection to other surfaces when the waste in the bags awaits sterilization and is moved to the sterilization site.

Accordingly, there is a need for a sterilization bag which can be fabricated without expensive additional equipment and which will prevent the microorganisms on the waste from contaminating other surfaces. There is a further need for a bag which adequately permits sterilization of the waste held by the bag to prevent the potential spread of infection after disposal.

SUMMARY OF THE INVENTION

The present invention provides a receptacle for handling contaminated waste for steam sterilization and subsequent disposal which includes a bag formed from an air and water impervious thermoplastic film. The film, preferably polypropylene, has means embedded therein to form pores therethrough upon exposure to steam sterilization. The pore forming means may be soluble materials which have been so coated with a web of the film that the soluble materials are stable at room temperature and swell upon exposure to steam sterilization thereby rupturing the webs to form the pores. The soluble materials can be either organic or inorganic in nature, such as polyvinyl alcohol, polyvinyl acetate, polyvinyl pyrrolidone and various salts, such as sodium chloride. The pore forming means may also be low molecular weight polymers such as carbowaxes, which are solid at room temperature and which melt upon exposure to steam sterilization thereby forming the pores.

The bag of the present invention holds the waste for sterilization and subsequent disposal. The bags may be variously sized to accommodate a range of contents. The pores which are formed upon exposure to steam sterilization permit the entrance of sterilant into and the exit of air from the bag for sterilization of the waste. The pores are preferably generally uniformly distributed in a quantity sufficient for sterilization of the waste without impairment of the structural integrity of the bag for disposal of the waste.

BRIEF DESCRIPTION OF THE DRAWINGS

The following detailed description of the preferred embodiment can better be understood if reference is made to the drawings in which:

FIG. 1 is a perspective view of the bag prior to use;

FIG. 2 is a perspective view of the bag ready to be sterilized;

FIG. 3 is a detailed view of a section of the bag following pore formation; and

FIG. 4 is a suggested method of handling contaminated waste using the bag of the present invention.

DETAILED DESCRIPTION OF THE PREFERRED EMBODIMENT

FIGS. 1 through 4 illustrate the preferred embodiment of the pore forming sterilization bag 10 of the present invention.

The bag 10 is made of a thermoplastic resin, preferably polypropylene, but any known heat resistant film forming polymer will suffice. Polypropylene is preferred for its high tensile strength at elevated temperatures, its low water vapor transmission and its economy of use. The polypropylene film 12 is embedded with additives (not shown) which will form pores 14 in the film 12 upon exposure to steam sterilization, as illustrated in FIG. 3.

The additives can be soluble materials or melt materials, such as the carbowaxes of polyethylene glycol. The soluble materials are selected from materials such as polyvinyl alcohol, polyvinyl acetate, polyvinyl pyrrolidone and various inorganic salts such as sodium chloride.

The film 12 is preferably manufactured by a blown film extrusion process, though any suitable known process may be used. The additives may be compounded with the polymer prior to or during the extrusion process in which the film 12 is formed. Compounding provides a homogenous mixture of polymer and additives. Pore 14 formation, therefore, is generally uniform throughout the film 12. The amount of additives embedded in the film 12 should be chosen so that a sufficient quantity of pores 14 can be formed to permit the entrance of sterilant into the bag 10 and the exit of air for the adequate sterilization of the waste held in the bag 10. The percentage of additive should be relatively low, however, to ensure the continued structural integrity of the bag 10 so that the bag 10 will adequately contain the waste 20 for disposal.

The soluble materials are preferably coated with a thin web of polypropylene or any other suitable thermoplastic resin chosen to make the bag 10. The web prevents the soluble material from readily dissolving at room temperature. When the film 12 is exposed to the elevated temperatures and moisture of the steam sterilization process, the soluble materials dissolve, thereby swelling and rupturing the web of polypropylene and thus forming distinct pores 14 in the film 12.

The carbowaxes melt in response to the elevated temperatures in the steam sterilization process, thus forming distinct pores 14. Those areas of film 12 which are not embedded with additives will not rupture or melt, thus maintaining the structural integrity of the bag 10.

Referring to FIGS. 1 and 2, bag 10 which is made from film 12, has exterior surface 15, opening 16 and interior surface 17. Referring to FIG. 4, bag 10 is preferably used by inserting the hand into opening 16, grasping the waste 20, such as a used petri dish as illustrated, with the bag 10 enclosed hand, turning the bag 10 inside out with the free hand so that the waste 20 is inside the bag 10 and closing the bag 10 with tie 18 or any suitable known closure. Exterior surface 15 is the only surface which touches the contaminated waste 20. Interior surface 17 is inverted and becomes the exterior surface. Since the film 12 is impervious to air and water, and, accordingly, to microorganisms, the surface 17 remains free from the contamination which might spread from its contents, waste 20, while the bag 10 and its contents await sterilization. When bag 10 is exposed to steam sterilization, pores 14 form in film 12. Sterilant can freely enter the bag 10 and air can escape bag 10. The waste 20 is thereby sterilized. At the end of the sterilization cycle, bag 10 and its contents, waste 20, may be safely disposed of.

The biohazard bag 10 may be variously sized to accommodate a range of contents. Frequently, the bag 10 will be the size of a trash bag to hold such items as patient dressings, garments and bulk laboratory waste. The large bags 10 permit the transport of bulk items while safeguarding against the spread of infection.

What is claimed is:

1. A receptacle for handling contaminated waste for steam sterilization and subsequent disposal comprising:
    a bag formed from an air and water impervious thermoplastic film, said film having means embedded therein to form pores therethrough upon exposure to steam sterilization.

2. A receptacle as recited in claim 1 wherein said pore forming means are soluble materials so coated with a web of said film that said soluble materials are stable at room temperature and swell upon exposure to steam sterilization thereby rupturing said webs to form said pores.

3. A receptacle as recited in claim 2 wherein said soluble materials are organic in nature.

4. A receptacle as recited in claim 2 wherein said soluble materials are inorganic in nature.

5. A receptacle as recited in claim 2 wherein said soluble materials are selected from the group consisting of polyvinyl alcohol, polyvinyl acetate, polyvinyl pyrrolidone and sodium chloride.

6. A receptacle as recited in claim 2 wherein said pore forming means are low molecular weight polymers which are solid at room temperature and which melt upon exposure to steam sterilization thereby forming said pores.

7. A receptacle as recited in claim 6 wherein said polymers are carbowaxes.

8. A receptacle as recited in claim 1 wherein said film is polypropylene.

9. A receptacle for handling contaminated waste for steam sterilization and subsequent disposal comprising:
    a polypropylene bag for holding the waste, said bag having means embedded therein to form pores therethrough upon exposure to steam sterilization, said pores permitting the entrance of sterilant into and the exit of air from said bag for sterilization of the waste.

10. A receptacle as recited in claim 6 wherein said pores are generally uniformly distributed in a quantity sufficient for sterilization of the waste without impairment of the structural integrity of said bag for disposal of the waste.

* * * * *